(12) United States Patent
Mihaylov et al.

(10) Patent No.: US 9,846,108 B2
(45) Date of Patent: Dec. 19, 2017

(54) CONTAINERS FOR FLUIDS WITH COMPOSITE AGILE WALLS

(71) Applicant: Nextteq, LLC, Tampa, FL (US)

(72) Inventors: Gueorgui Mihaylov, Virginia Beach, VA (US); Bryan Truex, Tampa, FL (US)

(73) Assignee: NEXTTEQ LLC, Tampa, FL (US)

( * ) Notice: Subject to any disclaimer, the term of this patent is extended or adjusted under 35 U.S.C. 154(b) by 0 days.

(21) Appl. No.: 15/254,150

(22) Filed: Sep. 1, 2016

(65) Prior Publication Data

US 2017/0049421 A1 Feb. 23, 2017

Related U.S. Application Data

(63) Continuation of application No. 13/028,620, filed on Feb. 16, 2011, now abandoned.

(60) Provisional application No. 61/304,904, filed on Feb. 16, 2010.

(51) Int. Cl.
| | |
|---|---|
| *G01N 1/12* | (2006.01) |
| *G01N 1/10* | (2006.01) |
| *G01N 1/22* | (2006.01) |
| *A61B 10/00* | (2006.01) |
| *B65D 30/08* | (2006.01) |
| *B65D 30/24* | (2006.01) |
| *B65D 30/10* | (2006.01) |

(52) U.S. Cl.
CPC ........... *G01N 1/10* (2013.01); *A61B 10/0096* (2013.01); *B65D 31/04* (2013.01); *B65D 31/14* (2013.01); *B65D 31/16* (2013.01); *G01N 1/22* (2013.01)

(58) Field of Classification Search
CPC ........ A61J 1/10; B01L 3/50; B01L 2200/026; B01L 5/02; G01N 1/00; G01N 1/10; G01N 1/14; G01N 1/22; G01N 1/24; G01N 1/1427; G01N 1/2247; G01N 1/2252

See application file for complete search history.

(56) References Cited

U.S. PATENT DOCUMENTS

| | | |
|---|---|---|
| 4,127,481 A | 11/1978 | Malchesky et al. |
| 4,161,179 A * | 7/1979 | Abramson ........... A61M 1/0011 128/DIG. 24 |
| 4,432,763 A | 2/1984 | Manschot et al. |

(Continued)

FOREIGN PATENT DOCUMENTS

| | | | |
|---|---|---|---|
| CN | 1835871 A | | 9/2006 |
| DE | 20115936 | * | 1/2002 |

(Continued)

OTHER PUBLICATIONS

English Translation of DE 20115936 Description, http://translationportal.epo.org/emtp/translate/?ACTION=description-retrieval&COUNTRY=DE&ENGINE=google&FORMAT=docdb&KIND=U1&LOCALE=en_EP&NUMBER=20115936&OPS=ops.epo.org/3.2&SRCLANG=de&TRGLANG=en, accessed on Mar. 26, 2017.*

(Continued)

*Primary Examiner* — Tatyana Zalukaeva
*Assistant Examiner* — Ariana Zimbouski
(74) *Attorney, Agent, or Firm* — Bernard G. Pike; Pike IP Law, PLLC

(57) ABSTRACT

The disclosure is directed to sampling bags having flexible walls. The sampling bags may have agile walls that include a shape memory component. The shape memory component tends to return the sampling bag to its initial shape. Such sampling bags may be used in a variety of sampling methods.

12 Claims, 10 Drawing Sheets

(56) References Cited

U.S. PATENT DOCUMENTS

| | | | |
|---|---|---|---|
| 4,657,541 | A | 4/1987 | Ichikawa et al. |
| 5,180,229 | A | 1/1993 | Niemeyer |
| 5,438,884 | A * | 8/1995 | Suddath .................. G01N 1/22 73/864.62 |
| 6,497,669 | B1 | 12/2002 | Kensey |
| 6,536,635 | B1 | 3/2003 | Garcia et al. |
| 6,613,036 | B1 | 9/2003 | Farmer et al. |
| 6,678,923 | B2 | 1/2004 | Goldberg et al. |
| 2001/0037627 | A1 | 11/2001 | Hausslein |
| 2002/0066712 | A1 | 6/2002 | Brockwell |
| 2002/0183652 | A1 | 12/2002 | Kensey |
| 2003/0228077 | A1 | 12/2003 | Laske |
| 2004/0048291 | A1 | 3/2004 | Hobolth |
| 2005/0249903 | A1 | 11/2005 | Kendig et al. |
| 2005/0286816 | A1 | 12/2005 | Laske |
| 2007/0269146 | A1 | 11/2007 | Jeannin |
| 2008/0302789 | A1 | 12/2008 | Stevenson |
| 2009/0032426 | A1 | 2/2009 | Tateishi et al. |
| 2009/0105629 | A1 | 4/2009 | Grant et al. |
| 2011/0118679 | A1 | 5/2011 | Bekele et al. |

FOREIGN PATENT DOCUMENTS

| | | |
|---|---|---|
| DE | 102006048754 | 4/2008 |
| JP | H01-80040 | 2/1991 |
| JP | 3005096 U | 12/1994 |
| JP | 10227725 A | 8/1998 |
| JP | 2000054452 A | 2/2000 |
| JP | 2001264222 A | 9/2001 |
| JP | 2007176491 A | 7/2007 |
| WO | 2004004904 A2 | 1/2004 |

OTHER PUBLICATIONS

"Colorimeter" definition, http://www.thefreedictionary.com/colorimetric, accessed Feb. 22, 2016.

Supplementary European Search Report for Appl. No. EP 11 74 5164 (PCT/US2011/025058) completed on Jun. 30, 2015 by the European Patent Office.

English Translation of Japanese Office Action dated Feb. 19, 2015 for corresponding Japanese Application No. 2012-553991.

Translation of DE102006048754.

Machine Translation of CN 1835871.

* cited by examiner

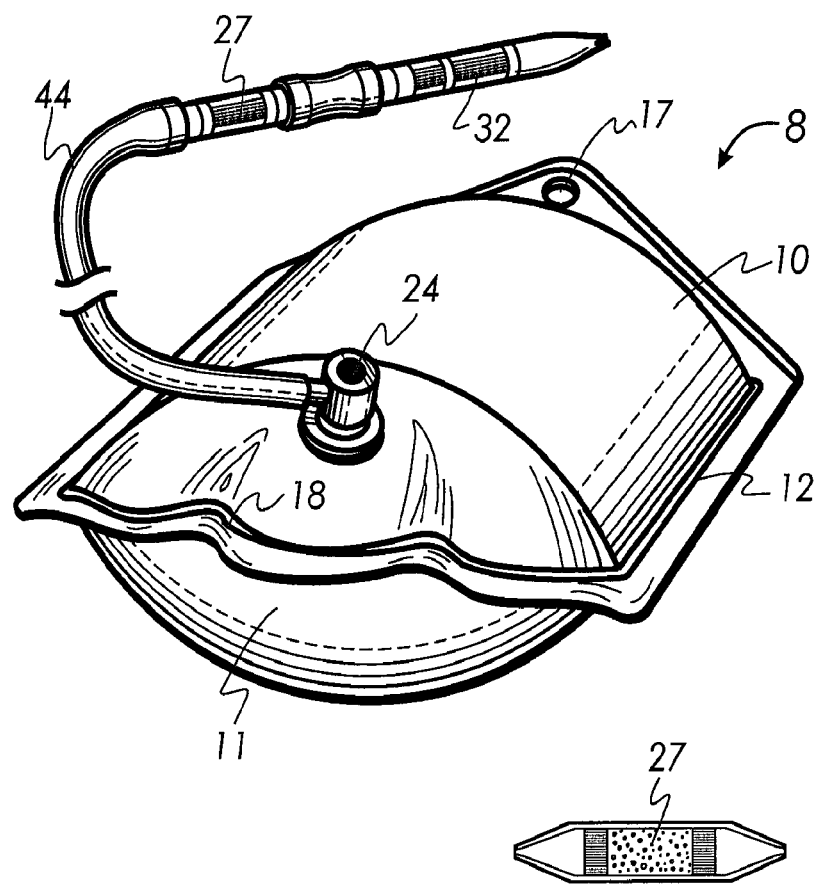
FIG.4
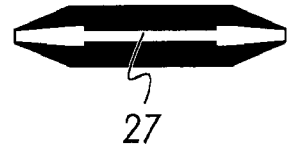

CONTAINERS FOR FLUIDS WITH COMPOSITE AGILE WALLS

RELATED APPLICATIONS

This application is a continuation application filed under 35 U.S.C. §120 claiming priority to U.S. patent application Ser. No. 13/028,620 having a filing date of Feb. 16, 2011 which claims priority under 35 U.S.C. §119 to U.S. Provisional Patent Application Ser. No. 61/304,904 filed on Feb. 16, 2010, both of which are incorporated by reference in their entirety.

FIELD OF THE INVENTION

Embodiments of the invention relate to containers for fluids, and more particularly to fluid containers comprising agile walls. The agile walls comprise a component with a shape memory that tends to return the fluid container to an initial shape. The sampling bags may be used for environmental sampling for industrial hygiene applications, for example.

BACKGROUND OF THE INVENTION

Conventional containers for fluids may have rigid walls or flexible walls. Containers with rigid walls have a defined permanent volume for containing fluids and containers with flexible walls have variable or changeable volumes. Conventional containers include, but are not limited to, bottles, canisters and bags. Such containers may be used for a variety of purposes, including obtaining and holding fluid samples and containing standard gas mixtures that may be used for calibration of analytical instruments. As used herein, the term "fluid" includes gases and/or liquids. There are many configurations of such containers that have been developed and specialized for particular uses.

Gas mixtures under pressure are effective for preparing standard fluid mixtures in industrial quantities and preferably with comparably high concentration of one (or more) components in a carrier fluid. Gas mixtures under high pressure are typically stored in containers with rigid walls. For laboratory use, such gas mixtures may be diluted with additional carrier fluid to a desired concentration of a specific component in order to prepare a standard mixture. Conventional containers for transporting, preserving and use of such standard mixtures may be containers having flexible walls comprised of an inert, low-permeability material. Materials having low sorption on the walls for the components contained are preferred to increase the integrity of the mixture. Containers with flexible walls, also referred to as sampling bags, are widely used for fluid sampling, air sampling and liquid sampling. Materials such as Kynar and Tedlar are widely used for making such containers.

In order to obtain a representative sample or prepare an accurate standard, the containers must be properly prepared prior to filling. Typically, the bags are flushed with neutral gas and subjected to high vacuum to substantially remove all the fluid from the container with strong vacuum pumps. The bags should be purged and flushed to cause desorption of any residue and their volume should reduced to substantially zero. Any adsorbed residue or residual gas may contaminate any prepared fluid mixture or sample of fluid put in a poorly prepared bag.

Containers with rigid walls and flexible walls both have their own advantages and disadvantages. The disadvantages of containers with rigid walls include their extremely high price and expensive maintenance; they are bulky and, thus, their storage, transportation, and mailing costs are expensive; they have to be over pressurized when delivery of gas vapors or mixtures is needed; and completely vacuumed before used for fluid sampling.

Another drawback of sampling with containers with rigid walls is that after removing a portion of the sample from the container, the pressure in the canister may be reduced below atmospheric pressure and additional carrier gas (noble gas for example) may be added to increase the pressure back to atmospheric pressure. This process dilutes the sample or standard and analysis requires compensation for the additional carrier gas.

One method of filling container with rigid walls is to create a vacuum within the container. The driving force to get fluid into the container is provided by this vacuum. A small sampling pump cannot create a sufficient vacuum within the container; therefore, strong specialized vacuum pumps are needed.

An alternative to the containers with rigid walls are containers with flexible walls or bags. For containers with flexible walls, two methods of filling are known and widely used: (OSHA Technical Manual—Directive Number: 08-05 (TED 01), Effective Jun. 24, 2008)

The first method comprises delivering the fluid or fluid sample, e.g. industrial ambient air, into the bag with an external pump. A schematic of this method is depicted in FIG. 8. The sampling method includes a bag 40, a pump 50 powered by a battery 52, and tubing 44 connecting pump 50 to bag 40. Typical personal sampling pumps are suitable for this sampling method.

Bags may be used for preparing standard fluid mixtures or for sampling. When preparing standard fluid mixtures, first the bag is filled with an appropriate measured volume of carrier fluid. The clean carrier gas is dosed with a quantity of fluid, typically, added by pump or syringe as shown in FIG. 8. When used for sampling, a sample of an environment is delivered through the pump and tubing into the bag. The bag is then sealed and sent to a laboratory for analysis.

There are advantages and disadvantages to using this method with sampling bags. The disadvantages include the cost, inaccuracy, and potential contamination from using an external pump to deliver and withdraw the fluid mix. The contamination or inaccuracy can occur from sorption and desorption of some chemicals or components of gas mixture or sample on the walls of the tubes, internal part of the pumps, filters, tubing and connectors. The same problem is caused by sorption of chemical components on the walls of the sampling bag. Even with cleaned walls, active adsorbing sites on the walls can reduce the concentration of certain chemicals when the sample gas is subsequently removed and analyzed. This adsorption may decrease the recovery of certain chemical compounds up to 15%. The recovery rates of this method can be improved with the use of expensive stationary pumps and connection tubes, especially for sampling of trace components.

These methods may also be improved by using a different configuration of pump and the sampling bag. In this configuration shown in FIG. 9, the flexible sampling bag 40 is hermetically sealed within an outer container 60 with rigid walls. The air from the outer container is evacuated through tubing 44 by a pump 50. The pump may be powered by battery 52. As the pressure in the outer container 60 is reduced and bag 40 expands and air from the surrounding environment enters the bag 40. Thus the vacuum outside of the bag 40 and within the container 60 is a driving force for fluid sampling. In the embodiment shown in FIG. 9, the inlet of a sampling bag is connected directly with the ambient fluid. This method does not suffer from one of the major drawbacks of the configuration shown in FIG. 8. The sample taken in the configuration of FIG. 9 does not contact the pump 50 or tubing 44, therefore, there is no sorption or cross-contamination from the walls of the tubing 44, connectors, filter or parts of the sampling pump 50. The other drawbacks of the configuration of FIG. 8 are, however, still persisting in the alternative configuration of FIG. 9, for example, the components is bulky and heavy; the equipment is expensive; the pump requires a battery and frequent maintenance; the sorption on the walls of the bag is the same as described above.

Various embodiments of these methods are described United States patents. For example, U.S. Pat. No. 3,866,474 to Hasselman describes a system in which a sample and an inert gas are drawn into a sample bag within a hermetically sealed container. U.S. Pat. No. 3,965,946 to D'Alo describes improvements in the construction of the outer container. U.S. Pat. No. 5,437,201 to Krueger describes a method of repeatedly purging the sampling bag within the outer container. More sophisticated devices are disclosed in U.S. Pat. No. 5,714,696 to Yemans. The devices attempt to overcome the disadvantages of the system to obtain samples with very low contamination levels. U.S. Pat. No. 6,338,282 to Gilbert describes an apparatus for collection of liquids proves the versatility of this approach. More recently U.S. Pat. No. 6,993,985 to Srebro describes using the apparatus combined in single device yet connected to external vacuum source. Despite of cleanliness suggested by this method, it is using comparably heavy, bulky and expensive equipment requiring calibration and battery maintenance.

An attempt to avoid using pumps in the sampling process is disclosed in U.S. Pat. No. 4,546,659 to Gill et al. This patent discloses a small (10 ml) envelope for the collection of atmospheric air samples for subsequent analysis. The envelope is formed of first and second opposed panels of flexible, gas impermeable material which are peripherally sealed to define a collection chamber. The envelope contains expandable means such as a spiral spring or foam. The expandable means transfer force to the walls via guard plate and large septum. These envelopes have several disadvantages. For example, the expandable means in contact with the sampled fluid increases the potential for adsorption by the inner elements, i.e. the spring or, especially, any foam. Further, the expandable means prevents full evacuation of the contents of the envelope. This large surface area for absorption allows only high concentrations of chemical compounds to be sampled with acceptable recovery and accuracy. Further, the envelope cannot be reused, because the sampling volume would need to be purged several times to clean the envelope, however, the self sealing septum of the envelope does not allow such a procedure.

There is a need for a sampling bag that is capable of fluid delivery or fluid sampling without an external source of energy such as pressure or vacuum pumps, without outer containers with rigid walls, without tubes, and tube connectors. Further there is a need for a sampling bag that creates it own driving force for sample collection. There is also a need for a sampling bag that reduces external contamination of a standard mixture or a sample.

There is a further need for a container for a standard mixture that does not require addition of further carrier gases and any associated concentration calculations and volume compensation related to the use of container with rigid walls.

There is further need for sampling bag that allows use of substantially all of the sampled volume. There is a further need for such a device that is inexpensive, easy to manufacture, designed for multiple uses, may be used with both sampling bags specially designed and conventional sampling bags, light, not bulky, capable of use by hand or may be self operated and easy to transport, and/or intrinsically safe in use.

SUMMARY OF THE INVENTION

Embodiments of the containers comprise flexible, agile walls. The flexible, agile walls have a tendency to return the container to initial configuration. The initial configuration may be a substantially fully expanded volume configuration, a substantially empty configuration or a partially full volume configuration. The agile walls may be deformed from the initial configuration by application of a force external to the sampling bag or a force internal to the sampling bag. The force may be a hand or weight pressing against one or both sides of the container to deform the bag from an initial expanded volume configuration (either partially or substantially full configuration) to a reduced volume configuration. When the force is removed the container has a tendency to return to the initial configuration due to a biasing force applied to the container by the agile walls. In most case, the agile walls will return the container to the original configuration if the interior volume of the container is capable of equalizing pressure between the interior and exterior of the container. The agile walls may comprise one or more component with a shape memory component that biases the sampling bag toward its initial configuration.

The walls of the container may comprise multiple layers or components. A layer may be a complete layer covering the substantially the entire surface area of the bag wall or a partial layer covering only a portion of the bag. The layer may be made of expanded metal, metal wire, leaf springs or other such configuration have an appropriate shape and shape memory. The agile walls provide a built-in regeneratable source of energy.

In one embodiment, the container comprises a composite wall. The composite wall may comprise multiple layers. The layers may include an interior layer and a shape memory layer. The interior layer may be any layer appropriate for the desired application, for a sampling container the interior layer may be flexible, low out-gassing, have very low sorption properties, and/or impermeability. The interior layer may comprise at least one of polyolefins polypropylene, polyethylene, polyfluorinated plastics, PTFE, Teflon, and other similar materials. Other layers of composite wall may comprise materials to provide addition properties to the over all structure. For example, a second layer may be less permeable to compound that the interior layer, thus increasing the impermeability of the composite wall. Another layer may comprise the shape memory component. The shape memory component may comprise at least on material selected from polycarbonates, acrylics, polyesters, metals or metal alloys, as well as other materials with a shape memory. In some embodiments, the layer comprising a shape memory component may be relatively thick compared to other layers of the composite.

A further layer or the interior layer may be a layer comprising materials with very or zero low permeability, such as stainless steel, nickel, -aluminum or other metallic layer that is flexible and sufficiently impermeable. In some embodiments, especially in embodiments wherein this layer is the interior layer, the metallic layer may comprise thin surface sub-layer or coating of chemically inert metal oxides. This metal oxide layer may also be siliconized. The layers may be in any appropriate order for the application in order to give the composite wall appropriate features.

A further optional layer may include an outer layer of the composite walls that comprises materials having certain properties, such as static dissipation, good adhesion to different materials, low friction and/or wear resistance, for example. Such outer layer may comprise at least one material selected from the group comprising metalized polyester, polyurethane, nylon, for example.

In certain embodiments, the shape memory component of the walls defines the main shape of the container in its initial configuration and the soft portion serves to conformably seal the container.

Embodiments of the container may have one of two typical initial configurations shapes, however, others are possible:

A container comprising a shape memory component with an initial flat configuration resulting in a container with a substantially zero volume between walls in its initial configuration. A container having a flat initial configuration is capable of being expanded by an increase in inner pressure, see FIG. 1-A. The shape memory component may be in an initial flat configuration or in an arcuate initial configuration. If the shape memory component is in an initial arcuate configuration, a container having a flat initial configuration may be formed by placing the shape memory components with the convex sides adjacent to each other, see a-1 of FIG. 1. The edges of the shape memory component are then secured together by the other layers of the container, see a-2 of FIG. 1A. If a fluid is added to the internal volume of the container, the shape memory component would be deformed as shown in a-3 of FIG. 1-A. In such an embodiment, the container will tend to deflate due to the tendency of the shape memory component to return to the initial flat configuration.

Another embodiment of the container having a inflated initial configuration comprising two arcuate shape memory components is shown in FIG. 1-B. In this embodiment, the arcuate shape memory components are placed with the concave side facing each other, see b-1 of FIG. 1-B. A force exerted on the exterior of the container may deflate the container as shown in b-2 of FIG. 1-B. The container will have a tendency to expand and draw fluid into the interior volume of the container, see b-3 of FIG. 1-B.

Embodiments of the containers with walls having an initially flat configuration walls tend to revert to the flat configuration after deformation, the exerting pressurizing forces on a fluid within the internal volume and is capable of expelling the fluid from the internal volume to zero volume. Such an embodiment may be used to provide external equipment with needed fluid flow or sample of the fluid within the volume—FIG. 1-A, a-1; a-2; a-3.

Embodiments of the container with an initial configuration with substantially fully expanded volume configuration or a partially full expanded configuration, may be forced to a flat shape with substantially zero internal volume. The agile walls having shape memory component will then exert pressure difference between the ambient environment and the inner space, thereby providing some driving force for fluid to fill the permanently expanded volume of the container-FIG. 1-B, b-1; b-2; b-3.

Embodiments of the present invention provides sampling bags which permit sampling without any additional devices and designs of sampling bags allowing self sampling. As used herein, self-sampling means sampling that once begun will continue without further assistance form the person taking the sample.

Other aspects and features of embodiments of the sampling bags comprising agile walls will become apparent to those of ordinary skill in the art, upon reviewing the following description of specific, exemplary embodiments of the present invention in concert with the figures. While features may be discussed relative to certain embodiments and figures, all embodiments can include one or more of the features discussed herein. While one or more particular embodiments may be discussed herein as having certain advantageous features, each of such features may also be integrated into various other of the embodiments of the invention (except to the extent that such integration is incompatible with other features thereof) discussed herein. In similar fashion, while exemplary embodiments may be discussed below as system or method embodiments it is to be understood that such exemplary embodiments can be implemented in various systems and methods. Further, U.S. Patent Application entitled "DEVICE FOR FLUID SAMPLING" filed on Feb. 16, 2011 in the name of the same inventors is hereby incorporated by reference in its entirety.

BRIEF DESCRIPTION OF THE DRAWINGS

FIG. 2-A Container with composite walls—showing permanent tendency to stay in flattened position creating overpressure in the chamber FIG. 2-B Container with composite walls—showing permanent tendency to stay in inflated defining inner space position creating underpressure in the chamber

DETAILED DESCRIPTION OF THE INVENTION

Figure 1A:
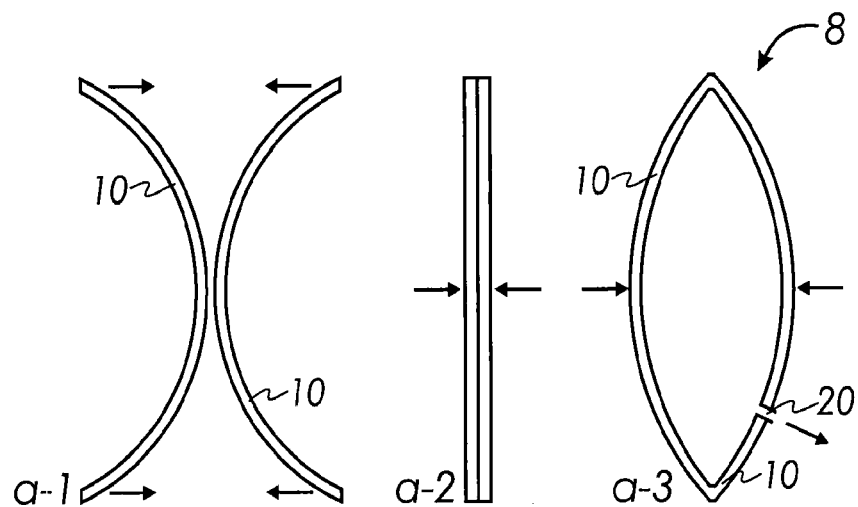
FIG. 1 Schematics of Composite agile walls with their memorized generic shape before and after assembly and the forces exerted by the agile walls FIG. 1-A, positions a-1; a-2; a-3; position a-1 walls before assembly; a-2 position of the walls after assembly and a-3 position of the walls after being pushed out FIG. 1-B, positions b-1, b-2, b-3; position of the walls before assembly b-1; after assembly b-2; expanded by agile walls to the permanent volume b-3
Figure 1B:
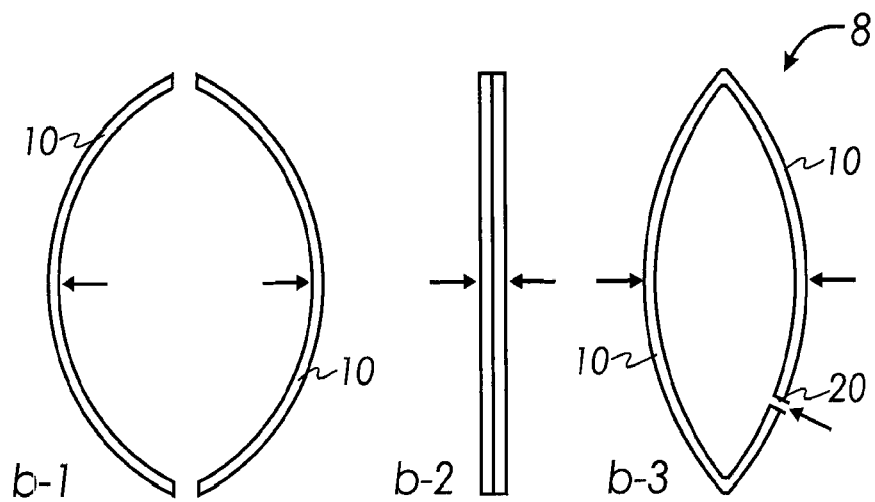

Embodiments of the sampling bags are shown in FIGS. 1A and 1B. The embodiments of the sampling bags comprise agile walls. The agile walls may be installed in different configurations in different embodiments to provide different forces. The agile walls comprise means for imparting motive forces to the walls of the sampling bag. In one embodiment, the agile walls may comprise at least one shape memory component. The shape memory component may be an component that provides a biasing force toward the initial configuration, such as a panel or leaf spring. In certain embodiments, the shape memory component is incorporated in the walls of the container. In some embodiments, the shape memory component may be incorporated into the container walls such that the shape memory component will not come in contact with the fluid within the container. In further embodiments, the shape memory component may be incorporated into the container such that the shape memory component does not prevent the container to be deflated such that the container has substantially zero internal volume. As used herein, "substantially zero internal volume" means that the internal volume may be compressed to less than 5% of the total volume of the substantially fully expanded volume of the container.

The motive forces or the shape memory component may bias the walls away from each other or towards each other depending upon the desired initial configuration or "home" configuration of the shape memory component as incorporated into the container. The shape memory component may be any component that may be deformed by a force and will returns substantially to its original shape when the force is removed. The shape memory component may be used to increase or decrease the volume in the bag as the shape memory component returns substantially to its original shape and the container returns to the initial configuration.

An embodiment of a sampling bag is shown in FIG. 1A. The shape memory components 15 have an original curved shape and are arranged with the convex sides adjacent to each other. Though not shown, the shape memory component may have be any shape including rectangular, square, triangular, circular, oval or other shape. Further, the shape memory component may be bowl shaped such that the center of the bowl may be forced flat and upon removal of the force the shape memory component will return substantially to its original bowl shape. For example, the embodiment of the sampling bag 8 shown in FIG. 2 comprises two generally rectangular shape memory components 15. In the embodiment of FIG. 2, the shape memory component occupies a substantial portion of the wall of the sampling bag 8. Alternatively, the shape memory component may comprise apertures, slats or ribs.

Returning to FIG. 1A, the shape memory components 10 may be incorporated into the walls of a container with flexible walls such that the shape memory components are pressed flat against each other as shown in FIG. 1A-a2. The configuration of the container will keep the shape memory components pressed flat against each other. If container shown on FIG. 1-A is filled with a fluid, the agile composite walls with shape memory will be distorted in a manner opposite of their original shape, compare FIGS. 1A-a1 to 1A-a3. Due to the shape memory of the agile walls, the shape memory component will have a tendency to return to its original shape and to expel the fluid out of the container through nozzle 20. Such an embodiment of the container will be very helpful when a source of a standard gas or gas mixture is necessary and may be used as a gas mixture delivery device for purpose of calibration of other apparatus. The direction of fluid moved by forces applied by the agile walls is shown by arrows.

Another embodiment of a container or sampling bag is shown in FIG. 1-B. In this embodiment, the two shape memory components in the agile walls are arranged with their convex sides adjacent to each other. In such an embodiment, the agile walls exert agile forces that tend to open the container, thus creating a moderate underpressure with in the container or sampling bag. This moderate underpressure creates a driving force for fluid to fill the container or sampling bag and complete the sampling without needs of external energy source. The direction of fluid moved by the forces expressed by agile walls is shown with arrow. The embodiments depicted in FIG. 1 demonstrates the versatility and variety of containers and sampling bags that may be designed with agile walls with their unique properties, replacing much more complicated systems for moving fluids. The shape of the shape memory component and the restriction of movement of the shape memory components due to the design of the agile walls create a sampling bag or container with a consistent fully filled volume.

FIG. 2-A shows a perspective view of an embodiment of a sampling bag with shape memory components similar to those shown in FIG. 1-B. The embodiment with agile walls is in flattened position whereby a force has acted upon the agile walls. The agile walls 10 of the sampling bag comprise shape memory components. In the embodiment of FIG. 2-A, the shape memory components are mounted inside composite material of the agile walls and do not overlap the entire area of the flattened wall. On the drawing two sides of this members are limited by dotted line and other two sides have common seam 12 with the other members of composite walls. In certain embodiments, the shape memory component will be sandwiched in between other layers of the multilayered agile walls.

Further on FIG. 3, the type of seams including or excluding shape memory component are explained in more detail. The shape memory components 15 of agile wall 10 of the embodiment shown in FIG. 2 are shown in cross section. The shape memory components 15 in this embodiment are substantially rectangular or with similar shape. Two opposite sides of walls 10 containing members 15 inside are in hinged or in movably sealed connection by seam 12. The end of the memory member 15 included partially in the wall 10 is shown on FIG. 2A with a dashed line. Thus, when the inlet/outlet 20 of the device is opened, fluid may enter and fill the underpressured space inside the device by movement of the shape memory components. In such an embodiment, the device takes substantially cylindrical shape as shown on FIG. 2-B. The side walls 11 not containing shape memory components 15 form the other two sides of the substantially cylindrical sampling volume. The agile forces of the walls 10 help to stretch tightly those side walls thereby defining every time, when device is full with fluid, the substantially same reproducible volume.

The embodiment of the container with agile walls of FIG. 2-B is shown in the open state with the shape memory components is the "relaxed" or original shape. In one embodiment of a method of sampling, the method of sampling comprises applying a force against the agile walls. When a force is applied to the agile walls, the sample bag is flattened and the volume inside the sample bag is reduced. Upon application of sufficient force, the volume in the sample bag may be reduced to almost zero and the fluid in the sample bag is substantially flushed out. Upon release of the force, the agile walls will return to their original shape. Repeatedly applying and removing forces to the agile walls allows the sample bag to be substantially completely flattened and then expanded thereby to purge the any contamination from the previous fluid contents.

Repeatedly purging the contents permits reaching a dynamic equilibrium of the sampled fluid mixture on the inside walls and removal of any chemical compounds absorbed on the interior walls of the sample bag. Such equilibrium cannot be obtained with any conventional sampling systems or methods for conventional sampling bags. Conventional sampling bags are filled only once by all known grab sampling methods.

The embodiment of the device of FIG. 2 is shown with generic inlet/outlet 20, but one skilled in the art can understand that any replacement of inlet/outlet 20 may be used. The inlet/outlet of embodiments of the container or sampling bags may have any desired design. Embodiments of the containers or sampling bags may have multiple inlets/outlets. The inlet/outlet may be specialized valves 22 or 24 may be used upon specific needs as shown in the Figures, for example.

Figure 2A:
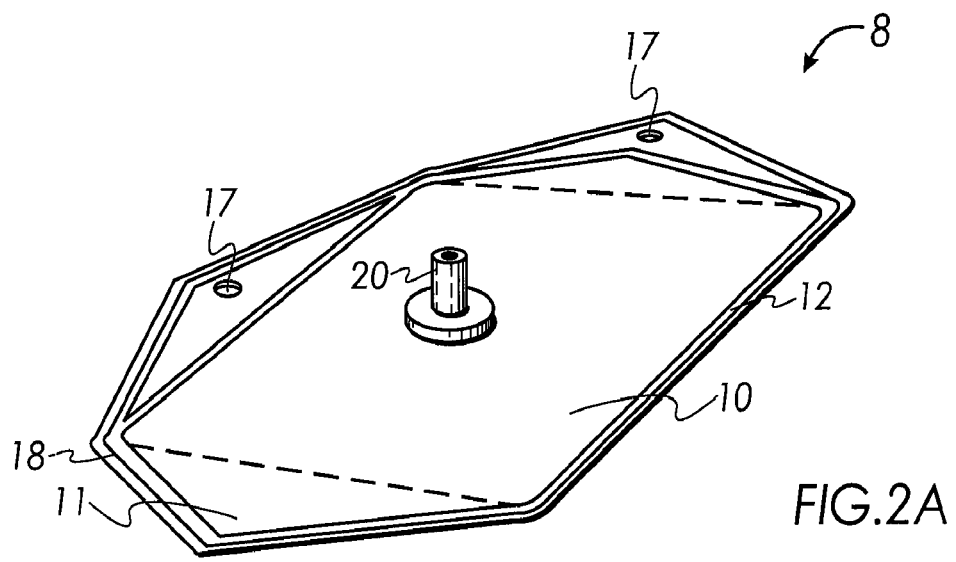
FIG. 2 Containers with composite walls
FIG. 2C depicts a shape memory component comprising two straight sides and two curved sides
FIG. 2D depicts a sampling bag comprising the shape memory component of FIG. 2C, the sampling bag is shown in a flattened state
FIG. 2E depicts a perspective view of the sampling bag shown in FIG. 2D in an expanded or filled state, the design of the shape memory component results in a "pillow"-shaped sampling bag with tightened and less wrinkles on the side walls FIG. 3 Cross-section of a multilayer agile wall including material with shape memory—Cross-section of seams: 3a—side walls; 3b—agile walls pivotably connected; 3c—agile walls with thinner portion as flexible hinge; 3d—agile walls with edges rotating in a profiled sleeve; 3e—agile walls with edges connected by loop FIG. 4 Container with connected in line sampling tube and flow restrictor FIG. 5 Container with connected in line colorimetric tube FIG. 6 Container with connected in line impingers FIG. 7 Container hanged on the belt for personal sampling in breathing zone—sampling device on the lapel FIG. 8 Schematic diagram of direct sampling with pump and sampling bag FIG. 9 Schematic diagram of indirect sampling with pump and sampling bag FIG. 10 Schematic diagram of indirect sampling with big hand driven syringe type pump and a sampling bag inside FIG. 11 Hard wall containers—canisters for vacuum sampling: a—0.4 L; b—15.00 L FIG. 12 Sampling pouch with internal move.
Figure 2B:
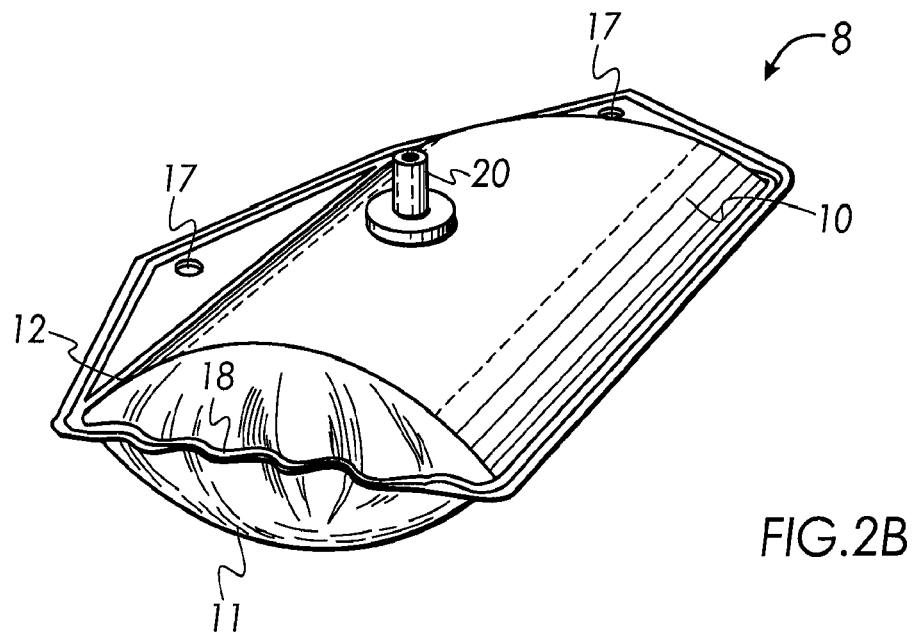
Figure 2C:
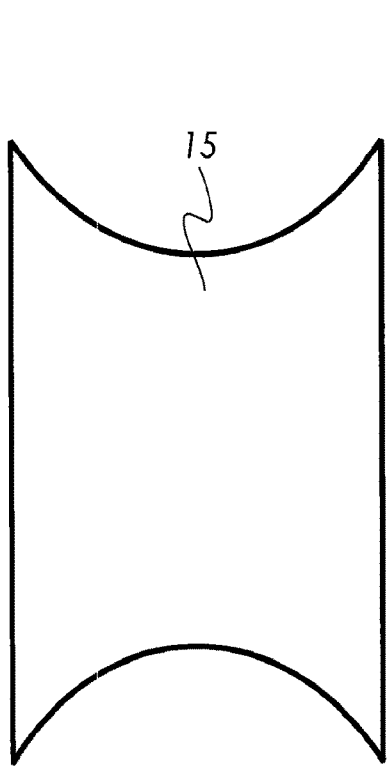
Figure 2D:
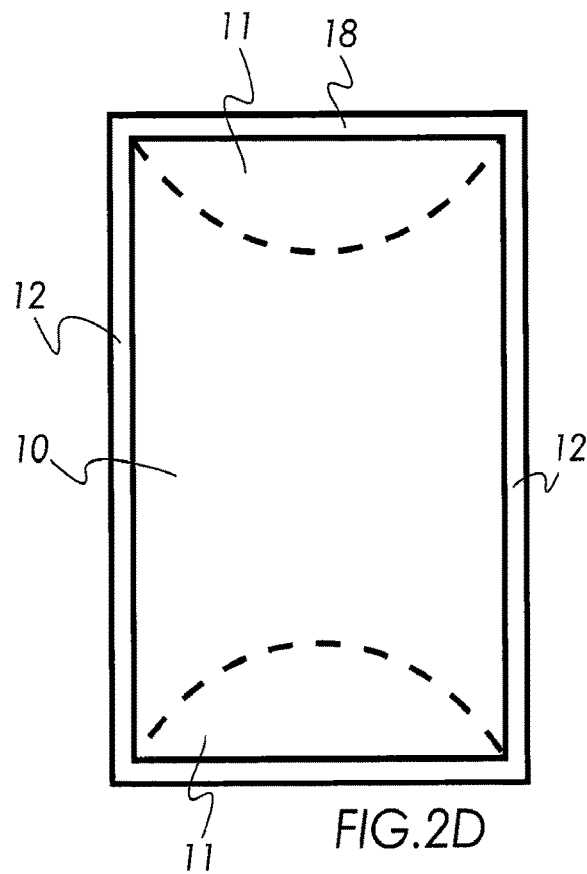
Figure 2E:
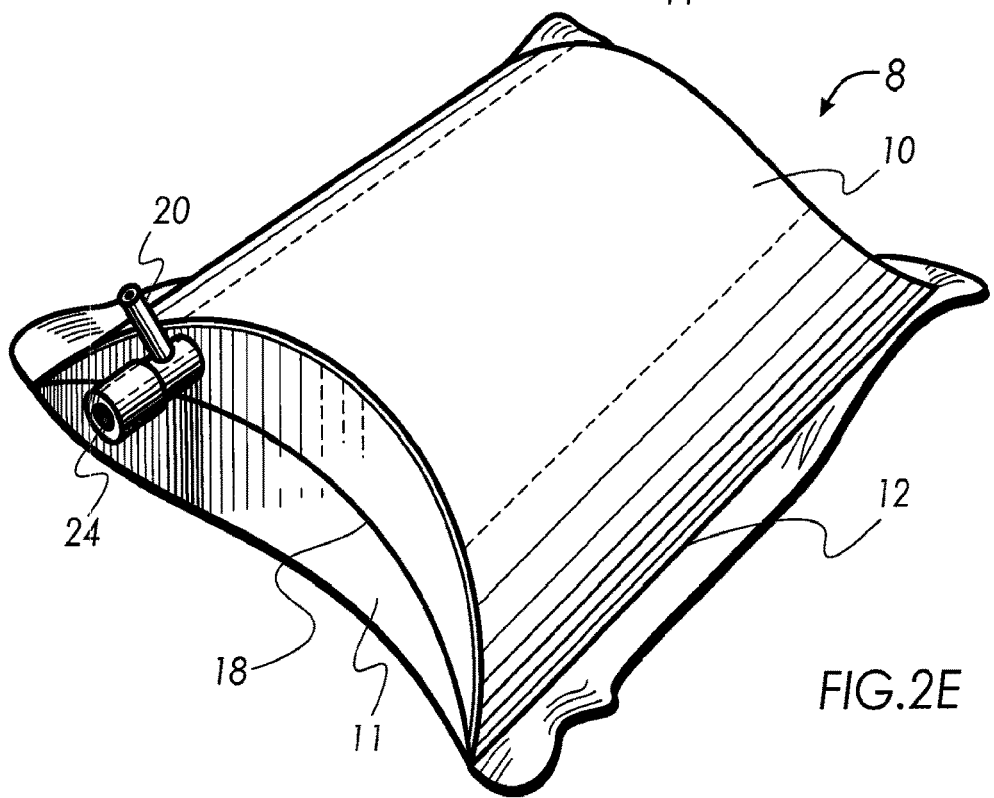
Figure 3A:
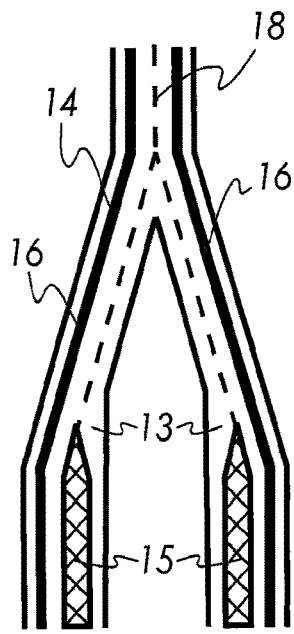
Figure 3C:
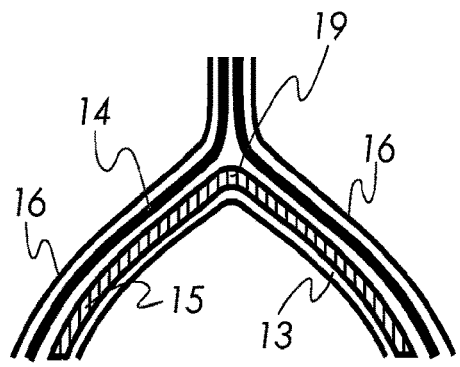
Figure 3D:
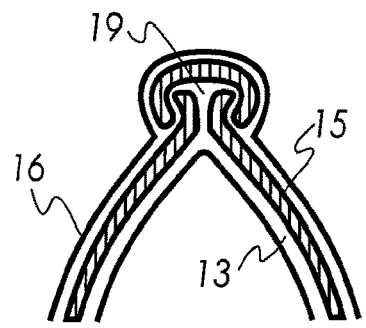
Figure 3B:
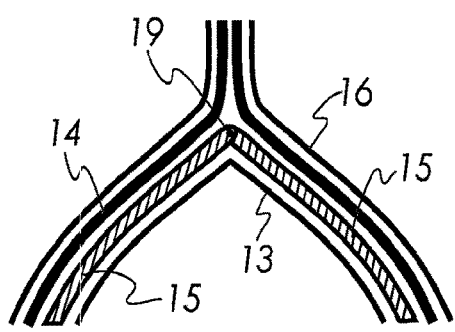
Figure 3E:
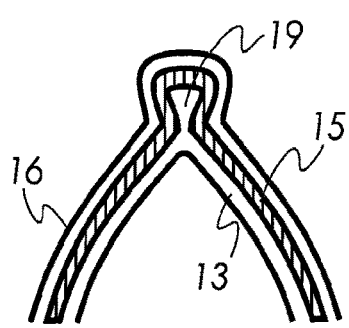
Figure 5:
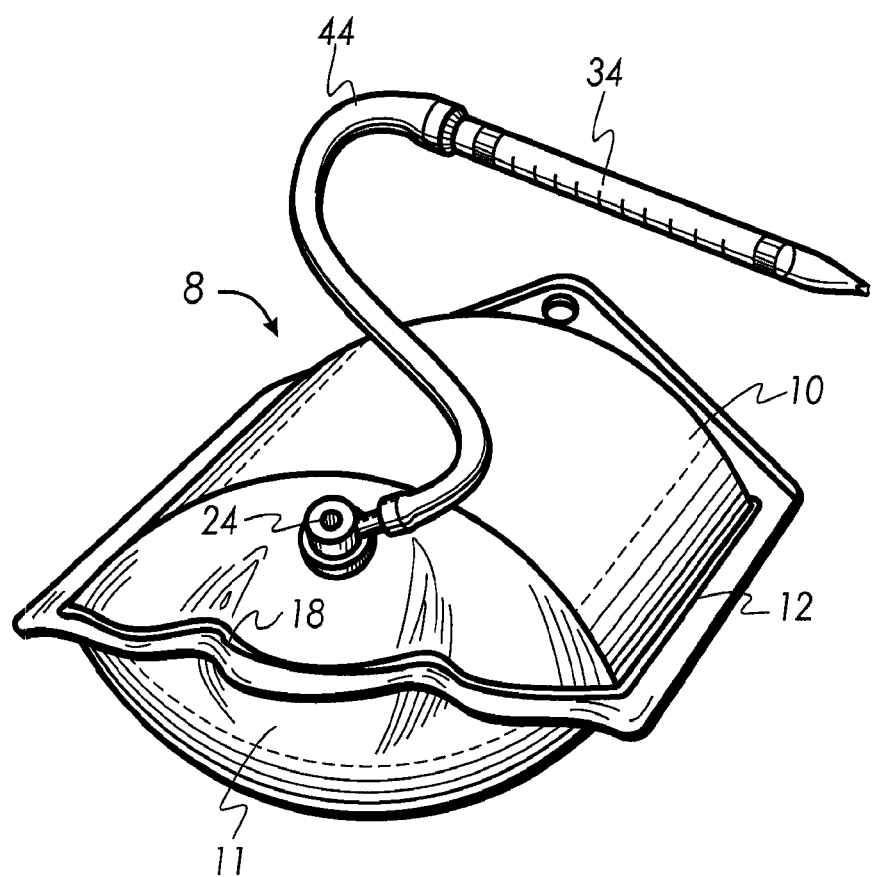
Figure 6:
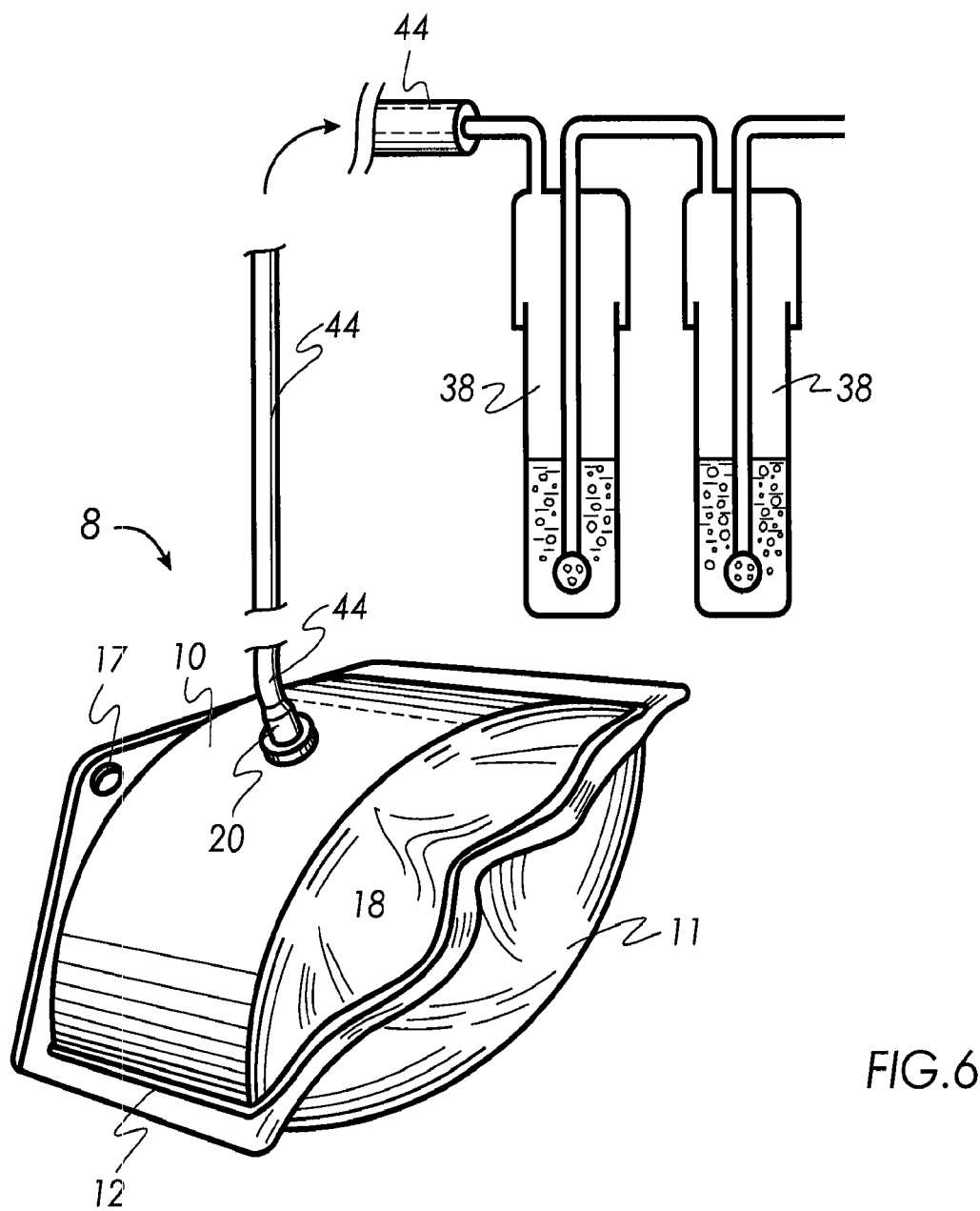
Figure 7:
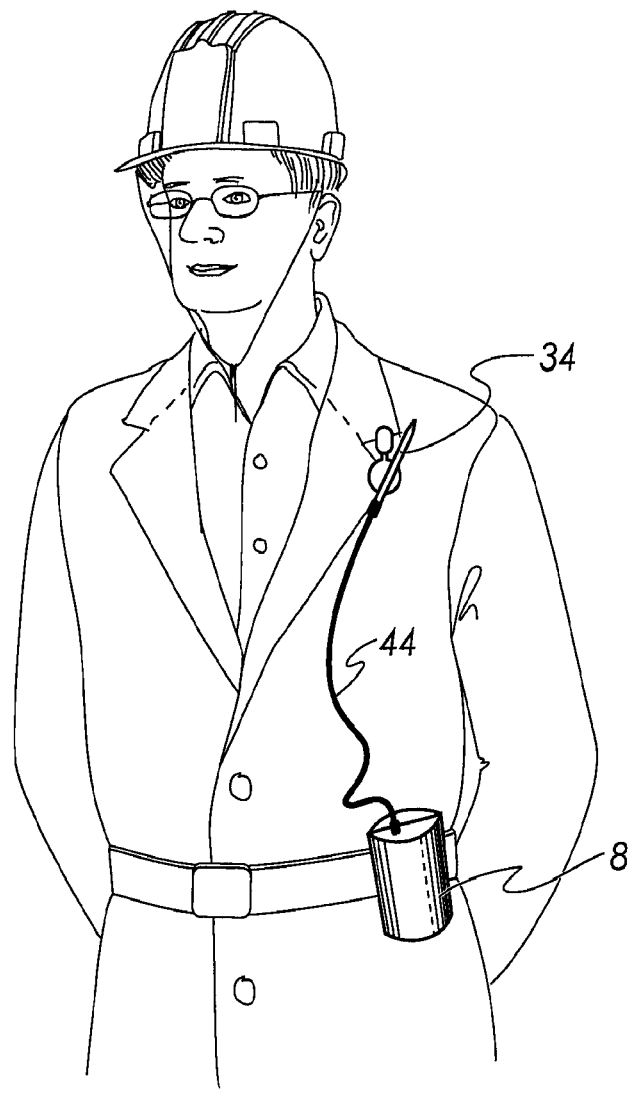
Figure 8:
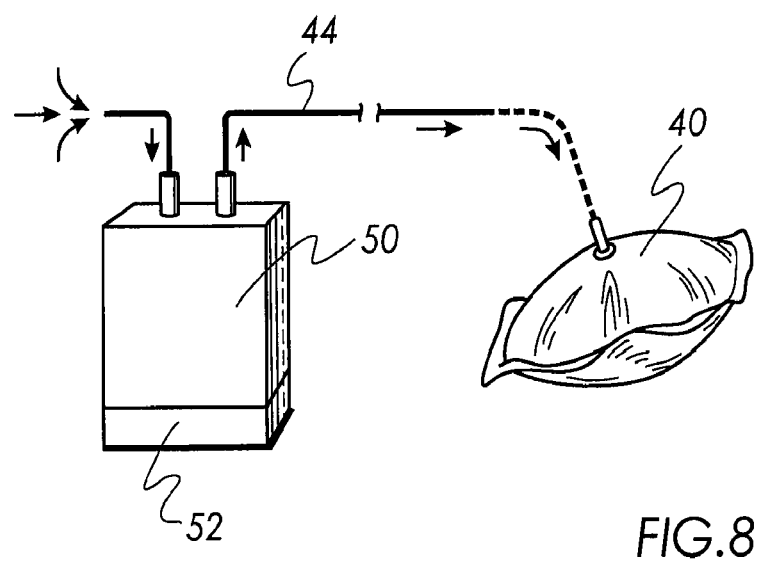
Figure 9:
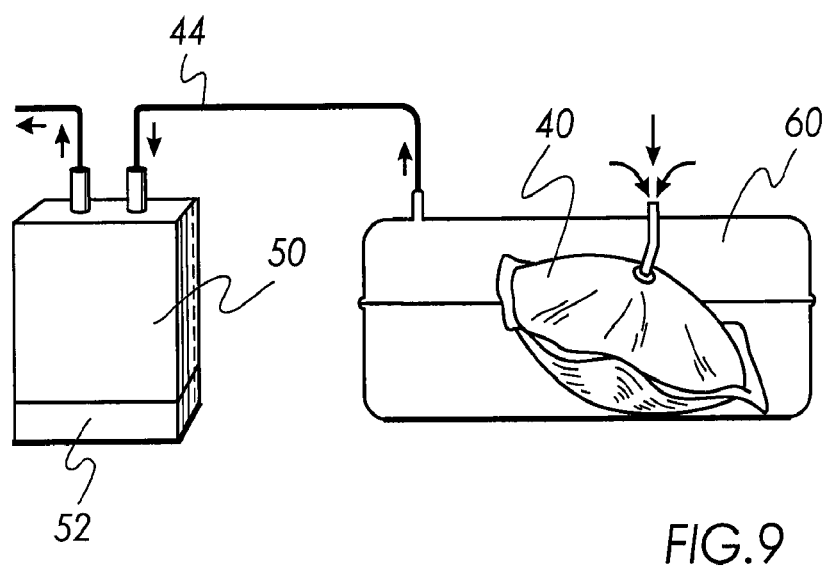
Figure 10:
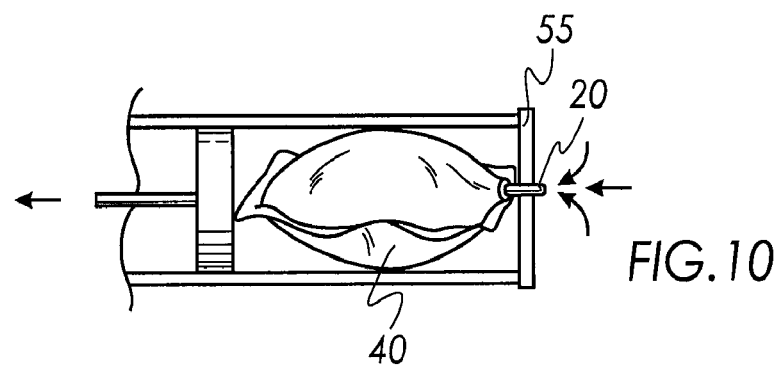
Figure 11:
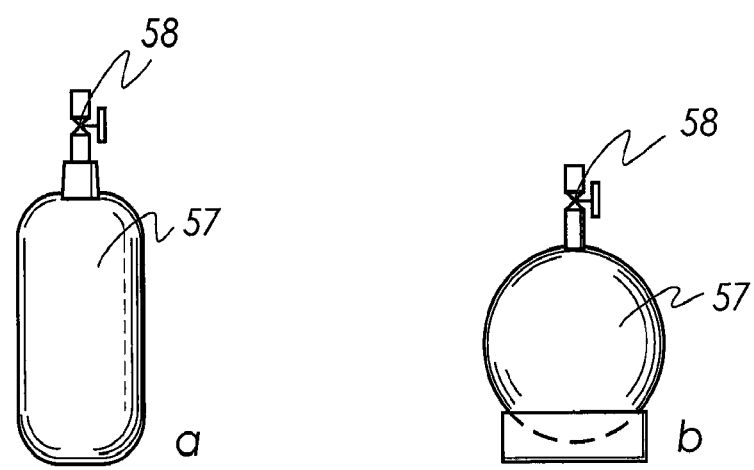
Figure 12:
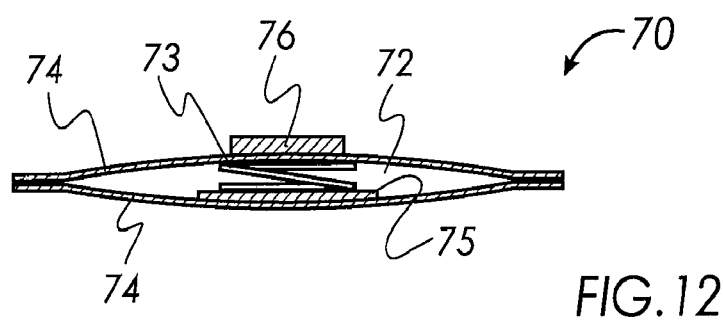

Embodiments of the container or sampling bag such as the embodiments shown in FIGS. 1A, 1B, 2A, and 2B are extremely simple and reliable when a direct grab sampling of a fluid such as air is needed. The ability to flush the device several times with sampled fluid has an enormous advantages compare to existing methods and devices. The pristine walls from low adsorbing materials used in any known device have a small amount of active sites capable of adsorption but they are in importance when the concentration of a targeted substance (contaminant) is comparably low, for example, in the parts per million (PPM) or parts per billion (PPB) range. Even in the freshly filled sampling bag assuming no diffusion through the walls, the recovery may be 85-90% due to sorption on the walls for the first fill of a sample bag. Recovery is defined as the percentage amount of the compound as indicated by analysis compared to the actual amount of the compound in the sampled environment. Thus, when the design upon the invention is in use and several flushes with sampled fluid are completed, this will lead to high recovery close to 100% for a given concentration, even low concentrations. In FIG. 2E, an embodiment of a shape memory component is depicted. The member expressing agile forces 15—FIG. 2-C has a shape similar to "pillow" shape with two parallel opposite sides. This shape when the bag 40 is completely inflated helps to have the soft side walls 11 well tightened without wrinkles thus defining a volume which is highly reproducible. The bag with reproducible volume is needed when the bag is intended to serve as a driving force for moderate underpressure. This shape may be advantageous and incorporated into the embodiments shown on FIGS. 4, 5, 6 and 7.

As already mentioned the device is shown with simple inlet/outlet 20 which can be replaced by appropriate valve 22 or 24 and/or connector or connecting line 44, as shown in FIGS. 4-7. Replacing the inlet/outlet port 20 with appropriate valve 22 or 24 (constructively not discussed here and after) having preset flow properties or being capable of flow regulation and adjustment may provide important features such as long term sampling—15, 30, 60 min or 8 hrs, for example, and ability to withdraw sample by a septum mounted directly into the valve or into its cap. Such valves are envisioned as having open/close functionality and/or the means to regulate the fluid flow. Such valves may be integral to the valve or interchangeable for different flow rates.

Different embodiments of portions of agile walls 10 are shown in FIG. 3. The cross section of the agile walls in FIG. 3-a of the agile wall upon present invention comprising a flat shape memory component 15 as well as a side seam 12 between two opposite sides of the opposite walls 10 including member 15. The other sides may have the same type of seam or may involve a direct connection between shape memory components 15. The embodiments of the portions of the agile walls shown in FIGS. 3b and 3c have a direct connection between the shape memory components. Such direct connection may comprise a thinner portion of the same flexible material shown on FIG. 3-c, may provide pivoted connection of edges of the material with shape memory shown on FIG. 3-b, another connection means, or a combination of connection means . . . . In these embodiments the shape memory component 15 is sandwiched between other members of composite agile wall 10. The shape memory component, however, may also be a either an inner layer or an outer layer of a composite agile wall or the agile wall may consist entirely of the shape memory component.

Embodiments of the containers or sample bags may be used for sampling over an extended period of time. The embodiments of the containers such as, but not limited to the embodiments shown in FIG. 1-B and FIG. 2 may provide a source of moderate underpressure in conjunction with other sampling devices. Some sampling devices require an especially small pressure difference for extended time period. As such a variety of long term sampling devices are given as example here and after. The embodiments depicted on FIG. 4, FIG. 5 and FIG. 6 comprise a sampling bag with agile walls. The sampling bag with agile walls comprise a certain volume when in the open or relaxed state in which no substantial forces are applied to the agile walls. In this open or relaxed position, the sampling bag with agile walls may comprise shape memory components that are not in their original positions. The agile walls prevent the shape memory components from completely returning to their original shape. However, the sampling bag in this position comprise side walls 11 that are tightly stretched and thus keeping the volume of the opened bag limited to a specific volume which may be reproducible. The shape of the shape memory component and the sampling bag walls may be modified to work together to produce a sampling bag may be flattened to reduce the volume and inflated to a reproducible volume. The embodiment of the sampling bag shown on FIG. 2-E comprises rectangular walls and a shape memory component combination capable of inflating to a structure having tightened side walls 11, therefore providing better reproducibility of the sampled volume. In the embodiment in FIG. 4, a sorbent containing sampling tube 32, such as one with charcoal or silica gel is coupled on the inlet 24 of the sampling bag. In this embodiment, a flow restrictor 27 is installed in the tubing 44 after the sampling tube 27. Flow restrictors are available that only allow a specific flow rate of fluid through them. The type of flow restrictor may adjust the appropriate sampling rate. Flow restrictor may be, for example, one of a group involving particulates flow resistor (filled with glass or ceramic powders), filter or membrane with known flow rate per unit area, or limited or critical orifices mounted conveniently in a tube 27 or directly in the valve 22 or 24. Sampling volumes from one up to several liters are easily achievable using this scheme. The use of flow restrictors 27 can serve the needs of medium (minutes to hrs) to long term sampling more than one working shift, one week or even one month. The big advantage is that not only no pumps flowmeter and other equipment are used, but that no person is involved in the sampling process. As such, some of these embodiments may be considered self-sampling devices. One person can perform long term sampling simultaneously at several different locations. Another big advantage is that the equipment may be designed easily intrinsically safety and used even in harsh environment were use of other equipment is problematic. Embodiments of the sampling devices may be self sampling devices. A self sampling device may be placed in a location and allowed to "self inflate" over a period of time. The sampling bag may be subsequently collected and sent for analysis.

A big advantage in all shown sampling designs is their versatility. The sampling may be set to predetermined volume, predetermined time of sampling, or when necessary to predetermined air flow using different flow restrictors. No flowmeter and pumps are needed.

The use of the basic designs of the containers of this invention is not limited only to sampling as explained herein and may be used in many cases including industrial or medical use when a moderate negative pressure difference is needed as driving force for the fluid flow.

Embodiments of the air sampling containers of both basic types upon present invention may have many unique features and consequently advantages compare to conventional sampling bags, for example, some embodiments have some or all of the features listed below:

No pumps of any type to expel or to fill fluids into container
No battery charging and maintenance
No pump calibration
Extreme simplicity of operation
Inexpensive sampling process
Higher recovery when sampling—in some applications, recovery may be close to 100%
Potentially reduced sorption on the walls of lines or inside pumps
Potentially reduced No cross-contamination
All directly sampled volume is usable compare to smaller part using canisters and bottles
Container is light and energy independent
Container is intrinsically safety and provides intrinsically safety sampling
Always ready for sampling
When empty with closed inlet, many containers can fit in relatively small volume portability is extremely important for field sampling.
Extremely versatile for sampling needs as follows:
The container can be used as primary sampling volume to store the sampled air, gas or gas mixture;
The container can be used as a primary source of driving force in conjunction with sorption sampling tubes at fixed sampling volume (sampling volumes from 10 ml to 5,000 even 10,000 ml are achievable);
The container can be used as a source of driving force in conjunction with colorimetric tubes, given the system container/tube is calibrated together at fixed sampling volume. Any restricted time 15 min STEL sampling or 30 min. Ceiling concentration or 480 min (all shift length) TWA or TLV sampling with predetermined volumes of 100, 200, 500 to >10000 ml/sample are achievable;
The container upon present invention can be calibrated in conjunction with filter cassettes for aerosols or liquid impingers for a predetermined sampled volume.

The embodiments of the described methods and sampling bags with agile walls are not limited to the particular embodiments, method steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:

1. A method of sampling a gas, comprising:
providing a sampling bag, wherein the sampling bag comprises agile walls having an initial configuration, wherein the initial configuration is a substantially fully expanded volume configuration and the agile walls comprise:
an interior flexible layer with two walls defining a closed inner sampling volume, wherein the interior flexible layer is selected from the group consisting of stainless steel, nickel and aluminum;
a memory shape member exterior to the inner flexible layer, such that the memory shape member will not come in contact with a sampled gas within the inner sampling volume and wherein, after applying a deformation of the memory shape member, the memory shape member provides a biasing force toward the initial configuration creating an underpressure and drawing the sampled gas into the inner sampling volume; and
a shut off valve;
applying a first force against the agile walls of the sampling bag with the shut off valve in an open position such that the inner sampling volume is reduced to substantially zero internal volume and fluid in the inner sampling volume is flushed out;
releasing the first force against the agile walls allowing the agile walls to return to their initial configuration;
applying a second force against the agile walls of the sampling bag with the shut off valve in the open position such that the inner sampling volume is reduced to substantially zero internal volume and fluid in the inner sampling volume is flushed out for a second time;
releasing the second force to draw a sample into the inner volume; and
moving the shut off valve to the closed position.

2. The method of claim 1, comprising applying and releasing a third force against the agile walls to purge the inner volume of any contamination from previous fluid contents of the inner volume to reach a dynamic equilibrium of the sampled fluid mixture on the inside walls and removal of any chemical compounds absorbed on the interior flexible layer of the sample bag.

3. The method of claim 1, comprising:
- a flow restrictor connected to the shut off valve, wherein the flow restrictor only allows a specific flow rate of the sampled gas through the flow restrictor and into the inner sampling volume; and
- a sampling tube connected to the flow restrictor such that the flow restrictor regulates the flow of the sampled gas to the specific flow rate through the sampling tube.

4. The method of claim 3, wherein the sampling tube is one of a sorbent containing sampling tube and a colorimetric tube.

5. The method of claim 4, wherein the sampling tube is a sorbent containing sampling tube and the sorbent is one of charcoal or silica gel.

6. The method of claim 1, wherein the initial shape of the memory shape member comprises either a U-shaped, V-shaped, circular, arcuate, or parabolic cross section.

7. The method of claim 1, wherein the memory shape member has a "pillow" shaped with two parallel side walls.

8. The method of claim 1, wherein the agile walls comprise an outer layer, wherein the outer layer comprises at least one material selected from the group consisting of nylon, polyurethane, and metalized polyester.

9. The method of claim 1, wherein the fluid container is configured such that the inner sampling volume is configured to be compressed to substantially zero internal volume.

10. The method of claim 3, comprising tubing connecting the valve to the flow restrictor.

11. The method of claim 3, comprising a septum mounted in the valve.

12. A method of sampling a gas, comprising:
providing a sampling bag, wherein the sampling bag comprises agile walls having an initial configuration, wherein the initial configuration is a substantially fully expanded volume configuration and the agile walls comprise:
- an interior flexible layer with two walls defining a closed inner sampling volume;
- a memory shape member exterior to the inner flexible layer, such that the memory shape member will not come in contact with a sampled gas within the inner sampling volume and wherein, after applying a deformation of the memory shape member, the memory shape member provides a biasing force toward the initial configuration creating an under-pressure and drawing the sampled gas into the inner sampling volume; and
- a shut off valve;

applying a first force against the agile walls of the sampling bag with the shut off valve in an open position such that the inner sampling volume is reduced to substantially zero internal volume;

releasing the first force against the agile walls allowing the agile walls to return to their initial configuration;

applying a second force against the agile walls of the sampling bag with the shut off valve in the open position such that the inner sampling volume is reduced to substantially zero internal volume;

releasing the second force to draw a sample into the inner volume; and moving the shut off valve to the closed position.

* * * * *